(12) United States Patent
Velculescu et al.

(10) Patent No.: US 7,504,493 B2
(45) Date of Patent: Mar. 17, 2009

(54) CHARACTERIZATION OF THE YEAST TRANSCRIPTOME

(75) Inventors: Victor E. Velculescu, Baltimore, MD (US); Bert Vogelstein, Baltimore, MD (US); Kenneth Kinzler, Bel Air, MD (US)

(73) Assignee: The John Hopkins University, Baltimore, MD (US)

( * ) Notice: Subject to any disclaimer, the term of this patent is extended or adjusted under 35 U.S.C. 154(b) by 758 days.

(21) Appl. No.: 10/915,727

(22) Filed: Aug. 11, 2004

(65) Prior Publication Data

US 2007/0031851 A1 Feb. 8, 2007

Related U.S. Application Data

(63) Continuation of application No. 09/335,032, filed on Jun. 16, 1999, now abandoned, which is a continuation-in-part of application No. 09/012,031, filed on Jan. 22, 1998, now abandoned.

(60) Provisional application No. 60/035,917, filed on Jan. 23, 1997.

(51) Int. Cl.
*C12N 15/11* (2006.01)
(52) U.S. Cl. ........................ 536/24.32; 435/6
(58) Field of Classification Search ........................ None
See application file for complete search history.

(56) References Cited

U.S. PATENT DOCUMENTS 5,556,752 A * 9/1996 Lockhart et al. ................ 435/6

FOREIGN PATENT DOCUMENTS

WO WO 98/32847 7/1998

OTHER PUBLICATIONS

Myers (GenBank® Accession No. G07433, Oct. 6, 1995).*
V.E. Velculescu et al. "Characterization of the yeast transcriptome" Cell, vol. 88, Jan. 24, 1997, pp. 243-251.
K. Nasmyth "Control of the yeast cells cycle by the Cdc28 protein kinase" Current Opinion in Cell Biology, vol. 5, No. 2, Apr. 1993, pp. 166-179.
D.K. Bishop et al. "DMC1: A Meiosis-Specific Yeast Homolog of *E. coli* RECA Required Forrecombination, Synaptonemal Complex Formation, and Cell Cycle Progression" Cell, vol. 69, May 1, 1992, pp. 439-456.
Y. Kyu Jang et al. "Differential expression of the rhp51+ gene, a recaA and RAD51 homolog from the fission yeast Schizosaccharomyces pombe" Gene, vol. 169, 1996, pp. 125-130.
J.H. Toyn et al. "The cell-cycle-regulated yeast gene DBF2, encoding a putative protein kinase, has a homologue that is not under cell-cycle control", Gene, vol. 104, 1991, pp. 63-70.
S.J. Elledge and R.W. Davis "DNA damage induction of ribonucleotide reductase" Mol. Cell. Biol., vol. 9, No. 11, Nov. 1989, pp. 4932-4940.
C. Frankhauser et al. "The *S. pombe* cdc15 gene is a key element in the reorganization of F-actin at mitose" Cell, vol. 82, Aug. 11, 1995, pp. 435-444.
N. Burns et al. "Large-Scale Analysis of Gene Expression, Protein Localization, and Gene Disruption, and Gene Disruption in *Saccharomyces cerecisiae*" Genes and Development, vol. 8, No. May 1, 1994 pp. 1087-1105.
C. Price et al. "A general approach to the isolation of cell cycle-regulated genes in the budding yeast, *Saccharomyces cerevisiae*" J. Mol. Biol, vol. 218, No. 3, Apr. 5, 1991, pp. 543-556.
V.E. Velculescu et al. "Serial Analysis of Gene Expression" Science, vol. 270, Oct. 20, 1995, pp. 484-487.
T. Yasugi and P.M. Howley "Identification of the structural and functional human homolog of the yeast ubiquitin conjugated enzyme UBC9" Nucleotic Acids Research, vol. 24, No. 11, 1996, pp. 2005-2010.
R.M. Goldsteyn et al. "Cell cycle analysis and chromosomal localizationof human Plk1, a putative homologue of the mitotic kinases *Drosophila polo* and *Saccharomyces cerevisiae* Cdc5" J. Cell Science, vol. 107, No. 6, pp. 1509-1517.
M. Schena et al. "Quantitative Monitoring of Gene expression Patterns with a Complementary DNA Microarray" Science, vol. 270, No. 5235, Oct. 20, 1995, pp. 467-470.
D.J. Lockhart et al. "Expression Monitoring by Hybridization to High-Density Oligonucleotide Arrays" Bio/Technology, vol. 14, No. 13, Dec. 1996, pp. 1675-1680.
D. Shalon et al. "A DNA Microarray System for Analyzing Complex DNA Samples Using Two-Color Fluorescent Probe Hybridization" Genome Research, vol. 6, No. 7, Jul. 1, 1996, pp. 639-645.
M. Schena et al. "Paralel human genome analysis: Microarray-based expression monitoring of 1000 genes" Proc. Natl. Acad. Sci., vol. 93, Oct. 1996, pp. 10614-10619.
Goffeau et al., Life with 600 Genes, Oct. 1996, Science, vol. 274 pp. 546-567.
Johnson, Mol. Gen. Genet. 238: 383 (1993).

* cited by examiner

*Primary Examiner*—James Martinell
(74) *Attorney, Agent, or Firm*—Banner & Witcoff, Ltd.

(57) ABSTRACT

Yeast genes which are differentially expressed during the cell cycle are described. They can be used to study, affect, and monitor the cell cycle of a eukaryotic cell. They can be used to obtain human homologs involved in cell cycle regulation. They can be used to identify antifungal agents and other classes of drugs. They can be formed into arrays on solid supports for interrogation of a cell's transcriptome under various conditions.

8 Claims, 5 Drawing Sheets

A

B

| Component | Virtual Rot (SAGE) %mRNA | Copies/cell | Rot (Reassociation) %mRNA | Copies/cell |
|---|---|---|---|---|
| 1 | 17 | 180 | 23 | 200 |
| 2 | 38 | 40 | 51 | 30 |
| 3 | 45 | 2.5 | 26 | 1.5 |

|       | 1 | 2 | 3 |
|-------|---|---|---|
| TDH2/3 | 519 | 561 | 636 |
| TEF1/2 | 396 | 229 | 379 |
| NORF1 | 114 | 84 | 182 |
| RNR4 | 9 | 111 | 7 |
| RNR2 | 9 | 85 | 9 |
| NORF5 | 0 | 49 | 0 |

FIGURE 5

CHARACTERIZATION OF THE YEAST TRANSCRIPTOME

This application is a continuation of application Ser. No. 09/335,032 filed Jun. 16, 1999, now abandoned which is a continuation-in-part of application Ser. No. 09/012,031 filed Jan. 22, 1998, now abandoned, which claimed priority to Ser. No. 60/035,917 filed Jan. 23, 1997.

This application incorporates by reference the sequence listing contained on each of two duplicate compact discs, which are part of the application file. The sequence listing is a 16,601 KB ASCII file named "Attorney Docket 001107.00494 sequence listing.txt," created on Jul. 29, 2004.

This invention was made with government support under CA57345 awarded by the National Institutes of Health. The government has certain rights in the invention.

TECHNICAL FIELD OF THE INVENTION

This invention is related to the characterization of the expressed genes of the yeast genome. More particularly, it is related to the identification and use of previously unrecognized genes.

BACKGROUND OF THE INVENTION

It is by now axiomatic that the phenotype of an organism is largely determined by the genes expressed within it. These expressed genes can be represented by a "transcriptome," conveying the identity of each expressed gene and its level of expression for a defined population of cells. Unlike the genome, which is essentially a static entity, the transcriptome can be modulated by both external and internal factors. The transcriptome thereby serves as a dynamic link between an organism's genome and its physical characteristics.

The transcriptome as defined above has not been characterized in any eukaryotic or prokaryotic organism, largely because of technological limitations. However, some general features of gene expression patterns were elucidated two decades ago through RNA-DNA hybridization measurements (Bishop et al., 1974; Hereford and Rosbash, 1977). In many organisms, it was thus found that at least three classes of transcripts could be identified, with either high, medium, or low levels of expression, and the number of transcripts per cell were estimated (Lewin, 1980). These data of course provided little information about the specific genes that were members of each class. Data on the expression levels of individual genes have accumulated as new genes were discovered. However, in only a few instances have the absolute levels of expression of particular genes been measured and compared to other genes in the same cell type.

Description of any cell's transcriptome would therefore provide new information useful for understanding numerous aspects of cell biology and biochemistry.

SUMMARY OF THE INVENTION

It is an object of the present invention to provide isolated DNA molecules and methods of using such molecules to affect the cell cycle and identify candidate drugs. These and other objects of the invention are achieved by providing the art with one or more of the embodiments described below.

According to one embodiment of the invention an isolated DNA molecule is provided. It comprises a coding sequence of a yeast gene selected from the group consisting of NORF genes comprising a SAGE tag as shown in SEQ ID NOS:67-811.

According to another embodiment of the invention a method of using NORF genes is provided. The method is for affecting the cell cycle of a cell. The method comprises the step of administering to a cell an isolated DNA molecule comprising a coding sequence of a NORF gene whose expression varies by at least 10% between any two phases of the cell cycle selected from the group consisting of log phase, S phase, and G2/M.

In yet another embodiment of the invention a method for screening candidate antifungal drugs is provided. The method comprises the steps of contacting a test substance with a yeast cell and monitoring expression of a NORF gene whose expression varies by at least 10% between any two phases of the cell cycle selected from the group consisting of log phase, S phase, and G2/M, wherein a test substance which modifies the expression of the yeast gene is a candidate antifungal drug.

In still another embodiment of the invention a method for identifying human genes which are involved in cell cycle progression is provided. The method comprises the step of contacting human DNA with a probe which comprises at least 14 contiguous nucleotides of a NORF gene whose expression varies by at least 10% between any two phases of the cell cycle selected from the group consisting of log phase, S phase, and G2/M. A human DNA sequence which hybridizes to the probe is identified as a sequence of a candidate human gene which is involved in cell cycle progression.

The present invention provides probes which comprise at least 14 contiguous nucleotides of a NORF gene comprising a SAGE tag as shown in SEQ ID NOS:67-811.

The invention also provides an array of probes on a solid support. At least one probe in the array comprises at least 14 contiguous nucleotides of a NORF gene comprising a SAGE tag as shown in SEQ ID NOS:67-811.

Still another embodiment of the invention is a method of identifying a candidate drug as a member of a class of drugs having a characteristic effect on gene expression in a yeast cell. A yeast cell is contacted with a candidate drug. Expression of at least one NORF gene whose expression is affected by the class of drugs is monitored in the yeast cell. Detection of a difference in expression of the at least one NORF gene relative to expression in the absence of the candidate drug identifies the candidate drug as a member of the class of drugs.

These and other embodiments of the invention which will be apparent to those of skill in the art upon reading the detailed disclosure provided below, make available to the art hitherto unrecognized genes, and information about the expression of genes globally at the organismal level.

BRIEF DESCRIPTION OF THE DRAWINGS

FIG. 5. Northern Blot Analysis of Representative Genes. TDH⅔, TEF½ and NORF1, are expressed relatively equally in all three states (lane 1, G2/M arrested; lane 2, S phase arrested; lane 3, log phase), while RNR4, RNR2, and NORF5 are highly expressed in S-phase arrested cells. The expression level observed by SAGE (number of tags) is noted below each lane and was highly correlated with quantitation of the Northern blot by PhosphorImager analysis ($r^2$=0.97).

TABLE LEGENDS

Figure 1:
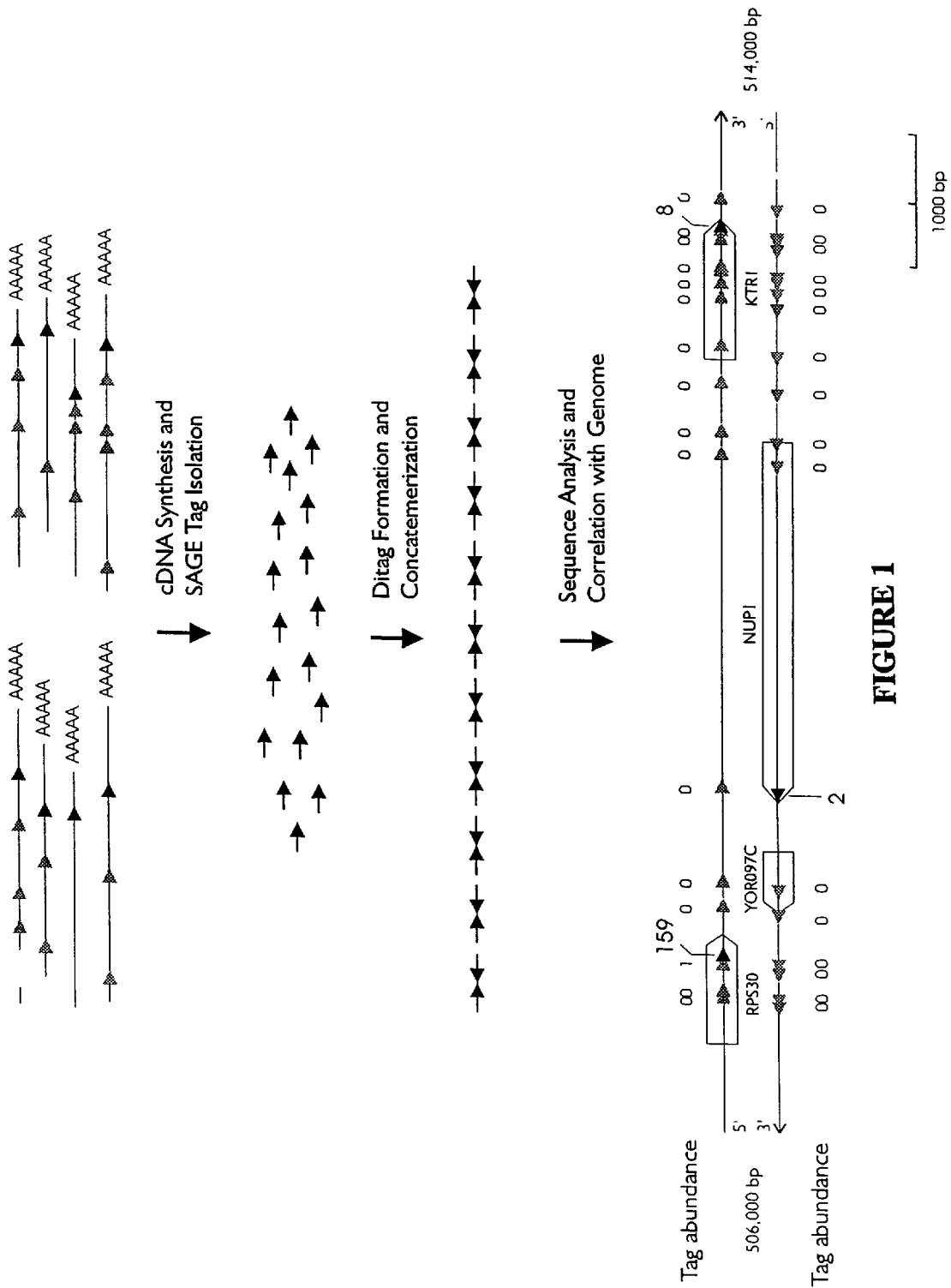
FIG. 1. Schematic of SAGE Method and Genome Analysis. In applying SAGE to the analysis of yeast gene expression patterns, the 3' most NlaIII site was used to define a unique position in each transcript and to provide a site for ligation of a linker with a BsmFI site. The type IIs enzyme BsmFI, which cleaves a defined distance from its non-palindromic recognition site, was then used to generate a 15 bp SAGE tag (designated by the black arrows), which includes the NlaIII site. Automated sequencing of concatenated SAGE tags allowed the routine identification of about a thousand tags per 36-lane sequencing gel. Once sequenced, the abundance of each SAGE tag was calculated, and each tag was used to search the entire yeast genome to identify its corresponding gene. The lower panel shows a small region of Chromosome 15. Gray arrows indicate all potential SAGE tags (NlaIII sites) and black arrows indicate 3' most SAGE tags. The total number of tags observed for each potential tag is indicated above (+ strand) or below (− strand) the tag. As expected, the observed SAGE tags were associated with the 3' end of expressed genes.

Table 1. Highly Expressed Genes. Tag represents the 10 bp SAGE tag adjacent to the NlaIII site; Gene represents the gene or genes corresponding to a particular tag (multiple genes that match unique tags are from related families, with an average identity of 93%); Locus and Description denote the locus name and functional description of each ORF, respectively; Copies/cell represents the abundance of each transcript in the SAGE library, assuming 15,000 total transcripts per cell and 60,633 ascertained transcripts.

Table 2. Expression of Putative Coding Sequences. Table column headings are the same as for Table 1.

Table 3. Expression of the most abundant NORF genes. SAGE Tag, Locus, and Copies/cell are the same as for Table 1; Chr and Tag Pos denote the chromosome and position of each tag; ORF Size denotes the size of the ORF corresponding to the indicated tag. In each case, the tag was located within or less than 250 bp 3' of the NORF.

Table 4. Expression of NORF genes. SAGE tag and Copies/cell are the same as for Table 1. Chr and Tag Pos denote the chromosome and position of each tag.

Table 5. Gene expression changes in different cell cycle phases. L denotes log phase; S denotes synthesis phase; G2/M denotes the mitotic phase. Tag Sequence represents the 10 bp SAGE tag adjacent to the NlaIII site; "ratio L to S" denotes the ratio of expression in log phase to expression in synthesis phase; "ratio S to G2/M" denotes the ratio of expression in synthesis phase to expression in G2/M phase; "ratio G2/M to L" denotes the ratio of expression in G2/M to log phase. #DIV/0! indicates an increase in expression from 0; a value of 0 indicates a decrease in expression to 0; a value of 1 indicates no change; a value less than 1 indicates a decrease in expression; and a value greater than 1 indicates an increase in expression.

Table 6. Intergenic open reading frames that contain or are adjacent to observed SAGE tags. Copies/cell represents abundance of each mRNA transcript as in Table 1. Positive expression level indicates the tag is on the + strand of the chromosome; Negative expression level indicates the tag is on the − strand.

DETAILED DESCRIPTION

It is a discovery of the present invention that certain hitherto unknown genes (the NORFs) exist and are expressed in yeast. These genes, as well as other previously identified and previously postulated genes, can be used to study, monitor, and affect phases of cell cycle. The present invention identifies which genes are differentially expressed during the cell cycle. Differentially expressed genes can be used as markers of phases of the cell cycle. They can also be used to affect a change in the phase of the cell cycle. In addition, they can be used to screen for drugs which affect the cell cycle, by affecting expression of the genes. Human homologs of these eukaryotic genes are also presumed to exist, and can be identified using the yeast genes as probes or primers to identify the human homologs.

New genes termed NORFs (not previously assigned open reading frames) have been found. They are uniquely identified by their SAGE tags. In addition their entire nucleotide sequences are known and publicly available. In general, these were not previously identified as genes due to their small size. However, they have now been found to be expressed.

Differentially expressed yeast genes are those whose expression varies by a statistically significant difference (to greater than 95% confidence level) within different growth phases, particularly log phase, S phase, and G2/M. Preferably the difference is at least 10%, 25%, 50%, or 100%. In some cases, differentially expressed genes are not expressed at detectable levels in one or more cell cycle phases as determined by SAGE analysis. Genes which have been found to have differential expression characteristics include: NORF № 1 (SEQ ID NO:12,220), 2 (SEQ ID NO:12,221), 4 (SEQ ID NO:12,222), 5 (SEQ ID NO: 12,223), 6 (SEQ ID NO:12,224), 17 (SEQ ID NO:12,225), 25 (SEQ ID NO:12,226), 27 (SEQ ID NO:12,227), TEF1/TEF2, EN02, ADH1, ADH2, PGK1, CUP1A/CUP1B, PYK1, YKL056C, YMR116C, YEL033W, YOR182C, YCR013C, ribonucleotide reductase 2 and 4, and YJR085C. Differential expression can be detected by any means known in the art, such as hybridization to specific probes or immunological assays.

Isolated DNA molecules according to the invention contain less than a whole chromosome and can be genomic or cDNA, i.e., lacking introns. Isolated DNA molecules can comprise a yeast gene or a coding sequence of a yeast gene involved in cell cycle progression, such as NORF genes which comprise SAGE tags as shown in SEQ ID NOS:67-811. Isolated DNA molecules which comprise yeast genes or coding sequences of yeast genes comprising SAGE tags as shown in SEQ ID NOS:37-12,203 are also isolated DNA molecules of the invention. Isolated DNA molecules can also consist of a yeast gene or a coding sequence of a yeast gene which comprises a SAGE tag as shown in SEQ ID NOS:37-12,203 or 67-811.

Any technique for obtaining a DNA of known sequence may be used to obtain isolated DNA molecules of the invention. Preferably they are isolated free of other cellular components such as membrane components, proteins, and lipids. They can be made by a cell and isolated, or synthesized using PCR or an automatic synthesizer. Methods for purifying and isolating DNA are routine and are known in the art.

To administer yeast genes to cells, any DNA delivery techniques known in the art may be used, without limitation. These include liposomes, transfection, mating, transduction, transformation, viral infection, electroporation. Vectors for particular purposes and characteristics can be selected by the skilled artisan for their known properties. Cells which can be used as gene recipients are yeast and other fungi, mammalian cells, including humans, and bacterial cells.

Antifungal drugs can be identified using yeast cells as described herein. Expression of a differentially expressed NORF gene can be monitored by any means known in the art. When a test substance modifies the expression of such a differentially expressed gene, for example by increasing or decreasing its expression, it is a candidate drug for affecting the growth properties of fungi and may be useful as an antifungal agent. Expression of more than one NORF gene can be monitored. For example, expression of 2, 3, 4, 5, 10, 15, 20, 30, 40, 50, 60, 75, 100, 150, 250, 300, 350, 400, 450, or 500 or more NORF genes can be monitored in single or multiple assays.

Because differentially expressed genes are likely to be involved in cell cycle progression, it is likely that these genes are conserved among species. The differentially expressed NORF genes identified by the present invention can be used to identify homologs in humans and other mammals by contacting DNA from these mammals with a probe which comprises at least 10 contiguous nucleotides of a differentially expressed NORF gene. The DNA can be genomic or cDNA, as is known in the art. Means for identifying homologous genes among different species are well known in the art. Briefly, stringency of hybridization can be reduced so that imperfectly matching sequences hybridize. This can be in the context of inter alia Southern blots, Northern blots, colony hybridization or PCR. Any hybridization technique which is known in the art can be used. A DNA sequence which hybridizes to the probe is identified as a sequence of a candidate gene which is involved in cell cycle expression.

Probes according to the present invention are isolated DNA molecules which have at least 10, and preferably at least 12, 14, 16, 18, 20, or 25 contiguous nucleotides of a particular NORF gene or other differentially expressed gene. The probes may or may not be labeled. They may be used, for example, as primers for PCR assays, or for detection of gene expression for Southern or Northern blots or in situ hybridization. Preferably the probes are immobilized on a solid support. The solid support can be any surface to which a probe can be attached. Suitable solid supports include, but are not limited to, glass or plastic slides, tissue culture plates, microtiter wells, tubes, or particles such as beads, including but not limited to latex, polystyrene, or glass beads. Any method known in the art can be used to attach the a probe to the solid support, including use of covalent and non-covalent linkages, passive absorption, or pairs of binding moieties attached respectively to the probe and the solid support.

More preferably, probes are present on an array so that multiple probes can simultaneously hybridize to a single biological sample. The probes can be spotted onto the array or synthesized in situ on the array. See Lockhart et. al., Nature Biotechnology, Vol. 14, December 1996, "Expression monitoring by hybridization to high-density oligonucleotide arrays." A single array contains at least one NORF probe, but can contain more than 100, 500 or even 1,000 different probes in discrete locations. If desired, one or more NORF probe(s) present on the array can be nucleotide sequences from a NORF gene which is differentially expressed during the cell cycle.

Genes identified by the present invention which are differentially expressed during the cell cycle can also be used to obtain gene expression profiles characteristic of the response of yeast genes of a yeast cell to a particular drug or class of drugs. Classes of drugs of particular interest for which gene expression profiles can be generated include those drugs which affect cell cycle or other cell processes, such as chemotherapeutic agents. If desired, gene expression profiles characteristic of more than one drug of a particular class can be generated and used to make a composite gene expression profile. For example, microtubule poison drugs such as vinblastin, taxol, vincristine, and taxotere can be used to generate gene expression profiles characteristic of microtubule poisons.

To generate a gene expression profile characteristic of a particular drug or class of drugs, a yeast cell is contacted with a particular drug or a member of a particular class of drugs. Expression of at least one yeast gene is monitored, either before and after contacting or in the contacted cell and in another yeast cell which has not been contacted with the drug. Genes which are monitored can be any yeast gene, including NORFS. Preferably, these genes are differentially expressed during the cell cycle. For example, yeast genes can be selected from genes comprising the SAGE tags shown in Tables 3, 4, 5, and 6 (SEQ ID NOS:67-12,203). If desired, genes such as NORF № 1, 2, 4, 5, 6, 17, 25, or 27, TEF1/TEF2, EN02, ADH1, ADH2, PGK1, CUP1A/CUP1B, PYK1, YKL056C, YMR116C, YEL033W, YOR182C, YCR013C, ribonucleotide reductase 2 and 4, and YJR085C, can be used for monitoring alterations in gene expression.

The expression of any number of these genes, such as 1, 2, 3, 4, 5, 10, 15, 20, 25, 30, 40, 50, 60, 75, 100, 150, 250, 500, 1000, 2000, 3000, 4000, 5000, or 5,500 genes, can be measured. It is particularly convenient to monitor expression of the differentially expressed genes using nucleic acids which are immobilized on a solid support or in an array, such as the gene arrays described above.

Many genes, particularly cell cycle genes, are likely to be conserved between yeast and mammals, including humans. Thus, gene expression profiles characteristic of a drug or class of drugs can be used to predict the effects of candidate drugs on human cells, by identifying the candidate drug as a member of a class of drugs whose characteristic gene expression profile is known. The candidate drugs can be pharmacologic agents already known in the art or can be compounds previously unknown to have any pharmacological activity. The candidate drugs can be naturally occurring or designed in the laboratory. They can be isolated from microorganisms, animals, or plants, and can be produced recombinantly or synthesized by chemical methods known in the art.

The effect of a candidate drug on expression of at least one gene whose expression is affected by the class of drugs is monitored. A gene expression profile obtained using the candidate drug which is similar to a gene expression profile for a particular drug or class of drugs identifies the candidate drug as a member of that class of drugs.

The effect of modifying particular substituents of a known drug or of a candidate drug can be similarly tested. Such methods are useful for determining whether alterations intended, for example, to increase solubility or absorption of a particular drug will have an unintended and possibly deleterious effect on genes which are differentially expressed during the cell cycle.

The above disclosure generally describes the present invention. A more complete understanding can be obtained by reference to the following specific examples which are provided herein for purposes of illustration only, and are not intended to limit the scope of the invention.

EXAMPLE

Summary

We have analyzed the set of genes expressed from the yeast genome, herein called the transcriptome, using serial analysis of gene expression (SAGE). Analysis of 60,633 transcripts revealed 4,665 genes, with expression levels ranging from 0.3 to over 200 transcripts per cell. Of these genes, 1,981 had known functions, while 2,684 were previously uncharacterized. Integration of positional information with gene expression data allowed the generation of chromosomal expression maps, identifying physical regions of transcriptional activity, and identified genes that had not been predicted by sequence information alone. These studies provide insight into global patterns of gene expression in yeast and demonstrate the feasibility of genome-wide expression studies in eukaryotes.

Results

Characteristics and Rationale of SAGE Approach

Several methods have recently been described for the high throughput evaluation of gene expression (Nguyen et al., 1995; Schena et al., 1995; Velculescu et al., 1995). We used SAGE (Serial Analysis of Gene Expression) because it can provide quantitative gene expression data without the prerequisite of a hybridization probe for each transcript. The SAGE technology is based on two basic principles (FIG. 1). First, a short sequence tag (9-11 bp) contains sufficient information to uniquely identify a transcript, provided that it is derived from a defined location within that transcript. Second, many transcript tags can be concatenated into a single molecule and then sequenced, revealing the identity of multiple tags simultaneously. The expression pattern of any population of transcripts can be quantitatively evaluated by determining the abundance of individual tags and identifying the gene corresponding to each tag.

Genome-Wide Expression

In order to maximize representation of genes involved in normal growth and cell-cycle progression, SAGE libraries were generated from yeast cells in three states: log phase, S phase arrested and G2/M phase arrested. In total, SAGE tags corresponding to 60,633 total transcripts were identified (including 20,184 from log phase, 20,034 from S phase arrested, and 20,415 from G2/M phase arrested cells). Of these tags, 56,291 tags (93%) precisely matched the yeast genome, 88 tags matched the mitochondrial genome, and 91 tags matched the 2 micron plasmid.

The number of SAGE tags required to define a yeast transcriptome depends on the confidence level desired for detecting low abundance mRNA molecules. Assuming the previously derived estimate of 15,000 mRNA molecules per cell (Hereford and Rosbash, 1977), 20,000 tags would represent a 1.3 fold coverage even for mRNA molecules present at a single copy per cell, and would provide a 72% probability of detecting such transcripts (as determined by Monte Carlo simulations). Analysis of 20,184 tags from log phase cells identified 3,298 unique genes. As an independent confirmation of mRNA copy number per cell, we compared the expression level of SUP44/RPS4, one of the few genes whose absolute mRNA levels have been reliably determined by quantitative hybridization experiments (Iyer and Struhl, 1996), with expression levels determined by SAGE. SUP44/RPS4 was measured by hybridization at 75+/−10 copies/cell (Iyer and Struhl, 1996), in good accord with the SAGE data of 63 copies/cell, suggesting that the estimate of 15,000 mRNA molecules per cell was reasonably accurate. Analysis of SAGE tags from S phase arrested and G2/M phase arrested cells revealed similar expression levels for this gene (range 52 to 55 copies/cell), as well as for the vast majority of expressed genes. As less than 1% of the genes were expressed at dramatically different levels among these three states (see below), SAGE tags obtained from all libraries were combined and used to analyze global patterns of gene expression.

Figure 2:
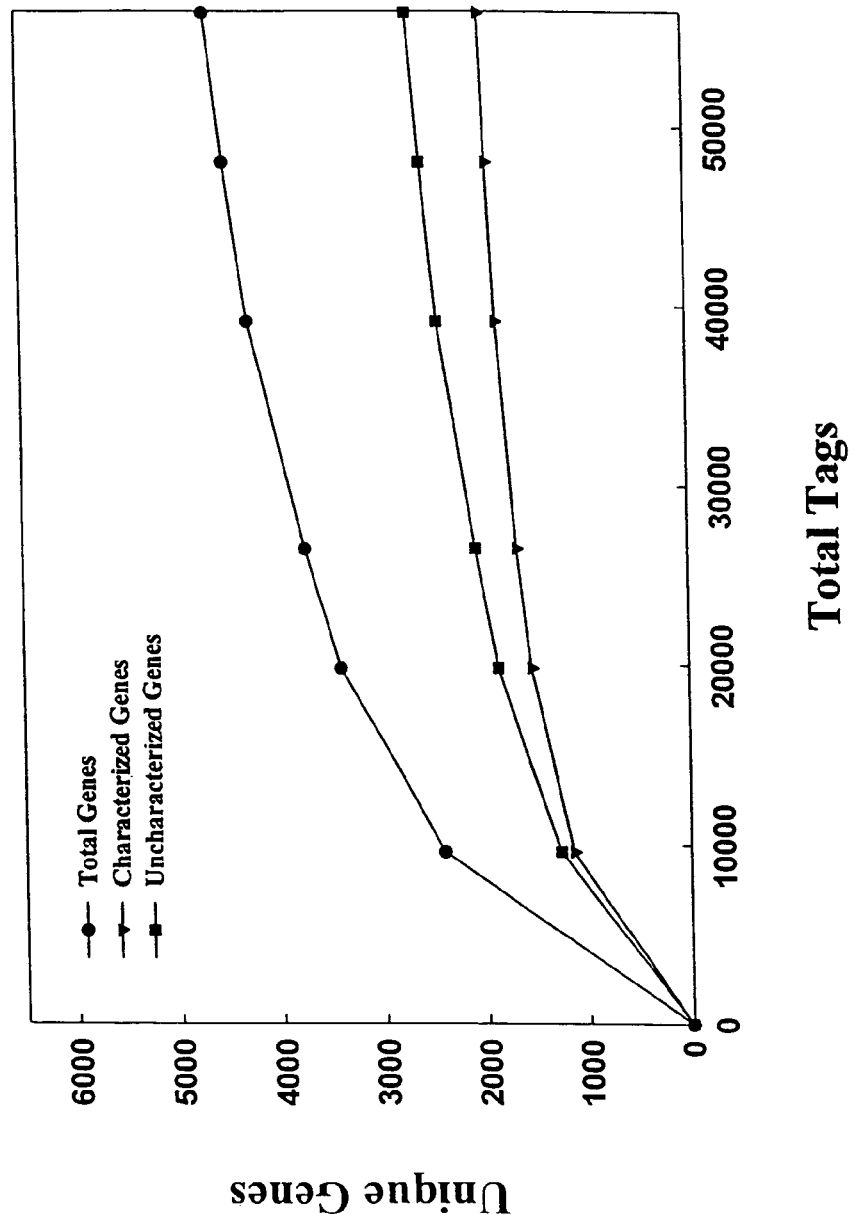
FIG. 2. Sampling of Yeast Gene Expression. Analysis of increasing amounts of ascertained tags reveals a plateau in the number of unique expressed genes. Triangles represent genes with known functions, squares represent genes predicted on the basis of sequence information, and circles represent total genes.

Analysis of ascertained tags at increasing increments revealed that the number of unique transcripts plateaued at ~60,000 tags (FIG. 2). This suggested that generation of further SAGE tags would yield few additional genes, consistent with the fact that sixty thousand transcripts represented a four-fold redundancy for genes expressed as low as 1 transcript per cell. Likewise, Monte Carlo simulations indicated that analysis of 60,000 tags would identify at least one tag for a given transcript 97% of the time if its expression level was one copy per cell.

The 56,291 tags that precisely matched the yeast genome represented 4,665 different genes. This number is in agreement with the estimate of 3,000 to 4,000 expressed genes obtained by RNA-DNA reassociation kinetics (Hereford and Rosbash, 1977). These expressed genes included 85% of the genes with characterized functions (1,981 of 2;340), and 76% of the total genes predicted from analysis of the yeast genome (4,665 of 6,121). These numbers are consistent with a relatively complete sampling of the yeast transcriptome given the limited number of physiological states examined and the large number of genes predicted solely on the basis of genomic sequence analysis.

Figure 3:
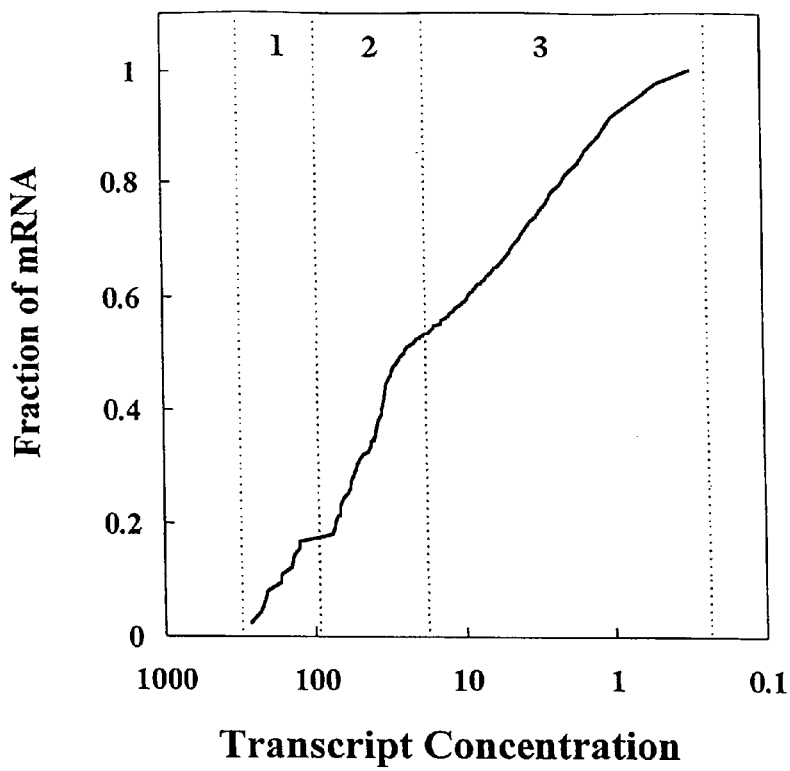
FIG. 3. Virtual Rot. (A) Abundance Classes in the Yeast Transcriptome. The transcript abundance is plotted in reverse order on the abscissa, whereas the fraction of total transcripts with at least that abundance is plotted on the ordinate. The dotted lines identify the three components of the curve, 1, 2, and 3. This is analogous to a Rot curve derived from reassociation kinetics where the product of initial RNA concentration and time is plotted on the abscissa, and the percent of labeled cDNA that hybridizes to excess mRNA is plotted on the ordinate. (B) Comparison of Virtual Rot and Rot Components. Transitions and data from virtual Rot components were calculated from the data in FIG. 3A, while data for Rot components were obtained from Hereford and Rosbash, 1977.

The transcript expression per gene was observed to vary from 0.3 to over 200 copies per cell. Analysis of the distribution of gene expression levels revealed several abundance classes that were similar to those observed in previous studies using reassociation kinetics. A "virtual Rot" of the genes observed by SAGE (FIG. 3A) identified three main components of the transcriptome with abundances ranging over three orders of magnitude. A Rot curve derived from RNA-cDNA reassociation kinetics also contained three main components distributed over a similar range of abundances (Hereford and Rosbash, 1977). Although the kinetics of reassociation of a particular class of RNA and cDNA may be affected by numerous experimental variables, there were striking similarities between Rot and virtual Rot analyses (FIG. 3B). Because Rot analysis may not detect all transcripts of low abundance (Lewin, 1980), it is not surprising that SAGE revealed both a larger total number of expressed genes and a higher fraction of the transcriptome belonging to the low abundance transcript class.

Integration of Expression Information with the Genomic Map

Figure 4:
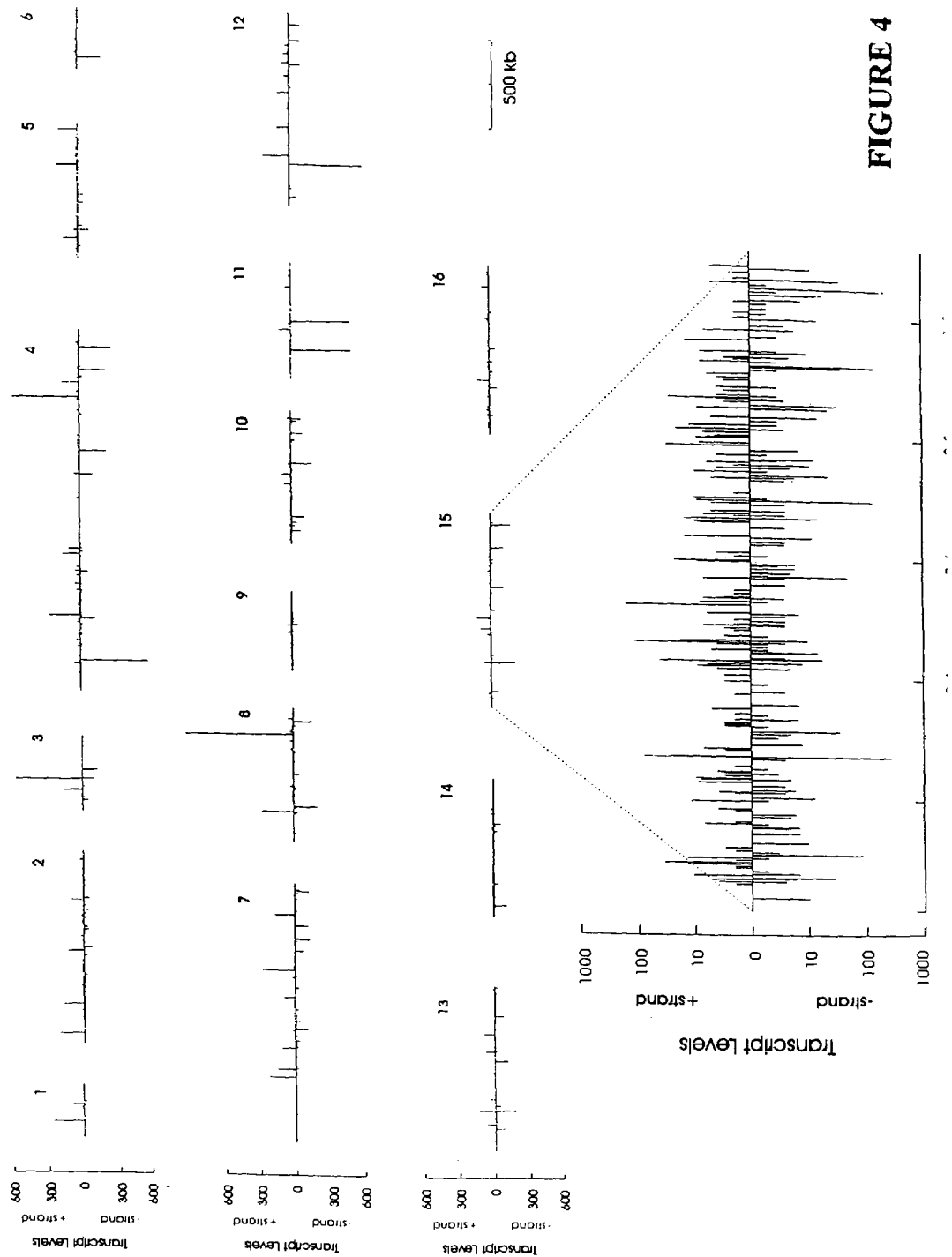
FIG. 4. Chromosomal Expression Map for S. cerevisiae. Individual yeast genes were positioned on each chromosome according to their open reading frame (ORF) start coordinates. Abundance levels of tags corresponding to each gene are displayed on the vertical axis, with transcription from the + strand indicated above the abscissa and that from the − strand indicated below. Yellow bands at ends of the expanded chromosome represent telomeric regions that are undertranscribed (see text for details).

The SAGE expression data could be integrated with existing positional information to generate chromosomal expression maps (FIG. 4). These maps were generated using the sequence of the yeast genome and the position coordinates of ORFs obtained from the Stanford Yeast Genome Database. Although there were a few genes that were noted to be physically proximal and have similarly high levels of expression, there did not appear to be any clusters of particularly high or low expression on any chromosome. Genes like histones H3 and H4, which are known to have coregulated divergent promoters and are immediately adjacent on chromosome 14 (Smith and Murray, 1983), had very similar expression levels (5 and 6 copies per cell, respectively). The distribution of transcripts among the chromosomes suggested that overall transcription was evenly dispersed, with total transcript levels being roughly linearly related to chromosome size ($r^2$=0.85, data not shown). However, regions within 10 kb of telomeres appeared to be uniformly undertranscribed, containing on average 3.2 tags per gene as compared with 12.4 tags per gene for non-telomeric regions (FIG. 4). This is consistent with the previously described observations of "telomeric silencing" in yeast (Gottschling et al., 1990). Recent studies have reported telomeric position effects as far as 4 kb from telomere ends (Renauld et al., 1993).

Gene Expression Patterns

Table 1 lists the 30 most highly expressed genes, all of which are expressed at greater than 60 mRNA copies per cell. As expected, these genes mostly correspond to well characterized enzymes involved in energy metabolism and protein synthesis and were expressed at similar levels in all three growth states (Examples in FIG. 5). Some of these genes, including ENO2 (McAlister and Holland, 1982), PDC1 (Schmitt et al., 1983), PGK1 (Chambers et al., 1989), PYK1 (Nishizawa et al., 1989), and ADH1 (Denis et al., 1983), are known to be dramatically induced in the glucose-rich growth conditions used in this study. In contrast, glucose repressible genes such as the GAL1/GAL7/GAL10 cluster (St John and Davis, 1979), and GAL3 (Bajwa et al., 1988) were observed to be expressed at very low levels (0.3 or fewer copies per cell).

As expected for the yeast strain used in this study, mating type a specific genes, such as the a factor genes (MFA1, MFA2) (Michaelis and Herskowitz, 1988), and alpha factor receptor (STE2) (Burkholder and Hartwell, 1985) were all observed to be expressed at significant levels (range 2 to 10 copies per cell), while mating type alpha specific genes (MFα1, MFα2, STE3) (Hagen et al., 1986; Kurjan and Herskowitz, 1982; Singh et al., 1983) were observed to be expressed at very low levels (<0.3 copies/cell).

Three of the highly expressed genes in Table 1 had not been previously characterized. One contained an ORF with predicted ribosomal function, previously identified only by genomic sequence analysis. Analyses of all SAGE data suggested that there were 2,684 such genes corresponding to uncharacterized ORFs which were transcribed at detectable levels. The 30 most abundant of these transcripts were observed more than 30 times, corresponding to at least 8 transcripts per cell (Table 2). The other two highly expressed uncharacterized genes corresponded to ORFs not predicted by analysis of the yeast genome sequence (NORF=Nonannotated ORF). Analyses of SAGE data suggested that there were at least 160 NORF genes transcribed at detectable levels. The 30 most abundant of these transcripts were observed at least 9 times (Table 3 and examples in FIG. 5).

Interestingly, one of the NORF genes (NORF5) was only expressed in S phase arrested cells and corresponded to the transcript whose abundance varied the most in the three states analyzed (>49 fold, FIG. 5). Comparison of S phase arrested cells to the other states also identified greater than 9 fold elevation of the RNR2 and RNR4 transcripts (FIG. 5). Induction of these ribonucleoside reductase genes is likely to be due to the hydroxyurea treatment used to arrest cells in S phase (Elledge and Davis, 1989). Likewise, comparison of G2/M arrested cells identified elevation of RBL2 and dynein light chain, both microtubule associated proteins (Archer et al., 1995; Dick et al., 1996). As with the RNR inductions, these elevated levels seem likely to be related to the nocodazole treatment used to arrest cells in the G2/M phase. While there were many relatively small differences between the states (for example, NORF1, FIG. 5), overall comparison of the three states revealed surprisingly few dramatic differences; there were only 29 transcripts whose abundance varied more than 10 fold among the three different states analyzed (Tables 4 and 5).

A comprehensive analysis for NORF genes was performed using the SAGE data. Yeast genome intergenic regions were defined as regions outside annotated ORFs or the 500 bp region downstream of annotated ORFs (yeast genome sequence and tables of annotated ORFs were obtained from SGD at the Stanford *Saccharomyces* genome website). Based on sequence analysis a total of 9524 putative ORFs of 25-99 amino acids were present in the intergenic regions; 510 of these ORFs contain or are adjacent to observed SAGE tags (Table 6). Of the 60,633 SAGE tags analyzed, there were 302 unique SAGE tags either within or adjacent to intergenic ORFs (100 bp upstream or 500 bp downstream of the ORF) (Table 6). Note that in some cases, more than one NORF contains or is adjacent to the SAGE tag. These tags matched the genome uniquely, were in the correct orientation, and were expressed at levels greater than 0.3 transcript copies per cell.

The expression level for each NORF shown in Table 6 corresponds to the number of mRNA transcript copies per cell. If the expression level is positive it means that the tag is on the + strand of the chromosome; if negative, the tag is on the − strand of the chromosome.

Discussion

Analysis of a yeast transcriptome affords a unique view of the RNA components defining cellular life. Comparison of gene expression patterns from altered physiologic states can provide insight into genes that are important in a variety of processes. Comparison of transcriptomes from a variety of physiologic states should provide a minimum set of genes whose expression is required for normal vegetative growth, and another set composed of genes that will be expressed only in response to specific environmental stimuli, or during specialized processes. For example, recent work has defined a minimal set of 250 genes required for prokaryotic cellular life (Mushegian and Koonin, 1996). Examination of the yeast genome readily identified homologous genes for 196 of these, over 90% of which were observed to be expressed in the SAGE analysis. Detailed analyses of yeast transcriptomes, as well as transcriptomes from other organisms, should ultimately allow the generation of a minimal set of genes required for eukaryotic life.

Like other genome-wide analyses, SAGE analysis of yeast transcriptomes has several potential limitations. First, a small number of transcripts would be expected to lack an NlaIII site and therefore would not be detected by our analysis. Second, our analysis was limited to transcripts found at least as frequently as 0.3 copies per cell. Transcripts expressed in only a minute fraction of the cell cycle, or transcripts expressed in only a fraction of the cell population, would not be reliably detected by our analysis. Finally, mRNA sequence data are practically unavailable for yeast, and consequently, some SAGE tags cannot be unambiguously matched to corresponding genes. Tags which were derived from overlapping genes, or genes which have unusually long 3' untranslated regions may be misassigned. Increased availability of 3' UTR sequences in yeast mRNA molecules should help to resolve the ambiguities.

Despite these potential limitations, it is clear that the analyses described here furnish both global and local pictures of gene expression, precisely defined at the nucleotide level. These data, like the sequence of the yeast genome itself, provide simple, basic information integral to the interpretation of many experiments in the future. The availability of mRNA sequence information from EST sequencing as well as various genome projects, will soon allow definition of transcriptomes from a variety of organisms, including human. The data recorded here suggest that a reasonably complete picture of a human cell transcriptome will require only about 10-20 fold more tags than evaluated here, a number well within the practical realm achievable with a small number of automated sequencers. The analysis of global expression patterns in higher eukaryotes is expected, in general, to be similar to those reported here for S. cerevisiae. However, the analysis of the transcriptome in different cells and from different individuals should yield a wealth of information regarding gene function in normal, developmental, and disease states.

Experimental Procedures

Yeast Cell Culture

The source of transcripts for all experiments was S. cerevisiae strain YPH499 (MATa ura3-52 lys2-801 ade2-101 leu2-Δ1 his3-Δ200 trp1-Δ63) (Sikorski and Hieter, 1989). Logarithmically growing cells were obtained by growing yeast cells to early log phase ($3 \times 10^6$ cells/ml) in YPD (Rose et al., 1990) rich medium (YPD supplemented with 6 mM uracil, 4.8 mM adenine and 24 mM tryptophan) at 30° C. For arrest in the G1/S phase of the cell cycle, hydroxyurea (0.1 M) was added to early log phase cells, and the culture was incubated an additional 3.5 hours at 30° C. For arrest in the G2/M phase of the cell cycle, nocodazole (15 μg/ml) was added to early log phase cells and the culture was incubated for an additional 100 minutes at 30° C. Harvested cells were washed once with water prior to freezing at −70° C. The growth states of the harvested cells were confirmed by microscopic and flow cytometric analyses (Basrai et al., 1996).

SAGE Protocol

The SAGE method was performed as previously described (Velculescu et al., 1995; Kinzler et al., U.S. Pat. Nos. 5,866,330 and 5,695,937), with exceptions noted below. PolyA RNA was converted to double-stranded cDNA with a BRL synthesis kit using the manufacturer's protocol except for the inclusion of primer biotin-5'-$T_{18}$-3'. The cDNA was cleaved with NlaIII (Anchoring Enzyme). As NlaIII sites were observed to occur once every 309 base pairs in three arbitrarily chosen yeast chromosomes (1, 5, 10), 95% of yeast transcripts were predicted to be detectable with a NlaIII-based SAGE approach. After capture of the 3' cDNA fragments on streptavidin coated magnetic beads (Dynal), the bound cDNA was divided into two pools, and one of the following linkers containing recognition sites for BsmFI was ligated to each pool: Linker 1,5'-TTTGGATTTGCTGGTG-CAGTACAACTAGGCTTAATAGGGACATG-3' (SEQ ID NO:1).5'-TCCCTATTAAGCCTAGTTGTACTGCAC-CAGCAAATCC [amino mod. C7]-3'(SEQ ID NO:2); Linker 2,5'-TTTCTGCTCGAATTCAAGCTTCTAAC-GATGTACGGGGACATG-3' (SEQ ID NO:3), 5'-TCCCCG-TACATCGTTAGAAGCTTGAATTCGAGCAG[amino mod. C7]-3' (SEQ ID NO:4).

As BsmFI (Tagging Enzyme) cleaves 14 bp away from its recognition site, and the NlaIII site overlaps the BsmFI site by 1 bp, a 15 bp SAGE tag was released with BsmFI. SAGE tag overhangs were filled-in with Klenow, and tags from the two pools were combined and ligated to each other. The ligation product was diluted and then amplified with PCR for 28 cycles with 5'-GGATTTGCTGGTGCAGTACA-3' (SEQ ID NO:5) and 5'-CTGCTCGAATTCAAGCTTCT-3' (SEQ ID NO:6), as primers. The PCR product was analyzed by polyacrylamide gel electrophoresis (PAGE), and the PCR product containing two tags ligated tail to tail (ditag) was excised. The PCR product was then cleaved with NlaIII, and the band containing the ditags was excised and self-ligated. After ligation, the concatenated products were separated by PAGE and products between 500 bp and 2 kb were excised. These products were cloned into the SphI site of pZero (Invitrogen). Colonies were screened for inserts by PCR with M13 forward and M13 reverse sequences located outside the cloning site as primers.

PCR products from selected clones were sequenced with the TaqFS DyePrimer kits (Perkin Elmer) and analyzed using a 377 ABI automated sequencer (Perkin Elmer), following the manufacturer's protocol. Each successful sequencing reaction identified an average of 26 tags; given a 90% sequencing reaction success rate, this corresponded to an average of about 850 tags per sequencing gel.

SAGE Data Analysis

Sequence files were analyzed by means of the SAGE program group (Velculescu et al., 1995), which identifies the anchoring enzyme site with the proper spacing and extracts the two intervening tags and records them in a database. The 68,691 tags obtained contained 62,965 tags from unique ditags and 5,726 tags from repeated ditags. The latter were counted only once to eliminate potential PCR bias of the quantitation, as described (Velculescu et al., 1995). Of 62,965 tags, 2,332 tags corresponded to linker sequences, and were excluded from further analysis. Of the remaining tags, 4,342 tags could not be assigned, and were likely due to sequencing errors (in the tags or in the yeast genomic sequence). If all of these were due to tag sequencing errors, this corresponds to a sequencing error rate of about 0.7% per base pair (for a 10 bp tag), not far from what we would have expected under our automated sequencing conditions. However, some unassigned tags had a much higher than expected frequency of A's as the last five base pairs of the tag (5 of the 52 most abundant unassigned tags), suggesting that these tags were derived from transcripts containing anchoring enzyme sites within several base pairs from their polyA tails. Given the frequency of NlaIII sites in the genome (one in 309 base pairs), approximately 3% of transcripts were predicted to contain NlaIII sites within 10 bp of their polyA tails.

As very sparse data are available for yeast mRNA sequences and efforts to date have not been able to identify a highly conserved polyadenylation signal (Irniger and Braus, 1994; Zaret and Sherman, 1982), we used 14 bp of SAGE tags (i.e. the NlaIII site plus the adjacent 10 bp) to search the yeast genome directly (yeast genome sequence obtained from the Stanford yeast genome ftp site [(genome-ftp.stanford.edu)] on Aug. 7, 1996, SEQ ID NOS:812-827). Because only coding regions are annotated in the yeast genome, and SAGE tags can be derived from 3' untranslated regions of genes, a SAGE tag was considered to correspond to a particular gene if it matched the ORF or the region 500 bp 3' of the ORF (locus names, gene names and ORF chromosomal coordinates were obtained from Stanford yeast genome ftp site, and ORF descriptions were obtained from MIPS www site on Aug. 14, 1996). ORFs were considered genes with known functions if they were associated with a three letter gene name, while ORFs without such designations were considered uncharacterized.

As expected, SAGE tags matched transcribed portions of the genome in a highly non-random fashion, with 88% matching ORFs or their adjacent 3' regions in the correct orientation (chi-squared P value $<10^{-30}$. In instances when more than one tag matched a particular ORF in the correct orientation, the abundance was calculated to be the sum of the matched tags. Tags that matched ORFs in the incorrect orientation were not used in abundance calculations. In instances when a tag matched more than one region of the genome (for example an ORF and non-ORF region) only the matched ORF was considered. In some cases the 15th base of the tag could also be used to resolve ambiguities.

For the identification of NORF genes, only tags were considered that matched portions of the genome that were further than 500 bp 3' of a previously identified ORF and were observed at least two times in the SAGE libraries.

Lengthy table referenced here

US07504493-20090317-T00001

Please refer to the end of the specification for access instructions.

Lengthy table referenced here

US07504493-20090317-T00002

Please refer to the end of the specification for access instructions.

Lengthy table referenced here

US07504493-20090317-T00003

Please refer to the end of the specification for access instructions.

Lengthy table referenced here

US07504493-20090317-T00004

Please refer to the end of the specification for access instructions.

Lengthy table referenced here

US07504493-20090317-T00005

Please refer to the end of the specification for access instructions.

Lengthy table referenced here

US07504493-20090317-T00006

Please refer to the end of the specification for access instructions.

REFERENCES

Archer, J. E., Vega, L. R., and Solomon, F. (1995). Rbl2p, a yeast protein that binds to beta-tubulin and participates in microtubule function in vivo. Cell 82, 425-434.

Bajwa, W., Torchia, T. E., and Hopper, J. E. (1988). Yeast regulatory gene GAL3: carbon regulation; UASGal elements in common with GAL1, GAL2, GAL7, GAL10, GAL80, and MEL1; encoded protein strikingly similar to yeast and *Escherichia coli* galactokinases. Mol Cell Biol 8, 3439-3447.

Basrai, M. A., Kingsbury, J., Koshland, D., Spencer, F., and Hieter, P. (1996). Faithful chromosome transmission requires Spt4p, a putative regulator of chromatin structure in *Saccharomyces cerevisiae*. Mol Cell Biol 16, 2838-2847.

Bishop, J. O., Morton, J. G., Rosbash, M., and Richardson, M. (1974). Three abundance classes in HeLa cell messenger RNA. Nature 250, 199-204.

Burkholder, A. C., and Hartwell, L. H. (1985). The yeast alpha-factor receptor: structural properties deduced from the sequence of the STE2 gene. Nucleic Acids Res 13, 8463-8475.

Chambers, A., Tsang, J. S., Stanway, C., Kingsman, A. J., and Kingsman, S. M. (1989). Transcriptional control of the *Saccharomyces cerevisiae* PGK gene by RAP1. Mol Cell Biol 9, 5516-5524.

Denis, C. L., Ferguson, J., and Young, E. T. (1983). mRNA levels for the fermentative alcohol dehydrogenase of *Saccharomyces cerevisiae* decrease upon growth on a nonfermentable carbon source. J Biol Chem 258, 1165-1171.

Dick, T., Surana, U., and Chia, W. (1996). Molecular and genetic characterization of SLC1, a putative *Saccharomyces cerevisiae* homolog of the metazoan cytoplasmic dynein light chain1. Mol Gen Genet 251, 38-43.

El-Deiry, W. S., Tokino, T., Velculescu, V. E., Levy, D. B., Parsons, R., Trent, J. M., Lin, D., Mercer, W. E., Kinzler, K. W., and Vogelstein, B. (1993). WAF1, a potential mediator of p53 tumor suppression. Cell 75, 817-825.

Elledge, S. J., and Davis, R. W. (1989). DNA damage induction of ribonucleotide reductase. Mol Cell Biol 9, 4932-4940.

Goffeau, A., Barrell, B. G., Bussey, H., Davis, R. W., Dujon, B., Feldmann, H., Galibert, F., Hoheisel, J. D., Jacq, C., Johnston, M., Louis, E. J., Mewes, H. W., Murakami, Y., Philippsen, P., Tettelin, H., and Oliver, S. G. (1996). Life with 6000 genes. Science 274, 546-567.

Gottschling, D. E., Aparicio, O. M., Billington, B. L., and Zakian, V. A. (1990). Position effect at *S. cerevisiae* telomeres: reversible repression of Pol II transcription. Cell 63, 751-762.

Hagen, D. C., McCaffrey, G., and Sprague, G. F., Jr. (1986). Evidence the yeast STE3 gene encodes a receptor for the peptide pheromone a factor: gene sequence and implications for the structure of the presumed receptor. Proc Natl Acad Sci USA 83, 1418-1422.

Hereford, L. M., and Rosbash, M. (1977). Number and distribution of polyadenylated RNA sequences in yeast. Cell 10, 453-462.

Irniger, S., and Braus, G. H. (1994). Saturation mutagenesis of a polyadenylation signal reveals a hexanucleotide element essential for mRNA 3' end formation in *Saccharomyces cerevisiae*. Proc Natl Acad Sci USA 91, 257-261.

Iyer, V., and Struhl, K. (1996). Absolute mRNA levels and transcriptional initiation rates in *Saccharomyces cerevisiae*. Proc Natl Acad Sci USA 93, 5208-5212.

Kurjan, J., and Herskowitz, I. (1982). Structure of a yeast pheromone gene (MF alpha): a putative alpha-factor precursor contains four tandem copies of mature alpha-factor. Cell 30, 933-943.

Leeds, P., Peltz, S. W., Jacobson, A., and Culbertson, M. R. (1991). The product of the yeast UPF1 gene is required for rapid turnover of mRNAs containing a premature translational termination codon. Genes Dev 5, 230 3-2314.

Lewin, B. (1980). Gene Expression 2, (New York, N.Y.: John Wiley and Sons), pp. 694-727.

McAlister, L., and Holland, M. J. (1982). Targeted deletion of a yeast enolase structural gene. Identification and isolation of yeast enolase isozymes. J Biol Chem 257, 7181-7188.

Michaelis, S., and Herskowitz, I. (1988). The a-factor pheromone of *Saccharomyces cerevisiae* is essential for mating. Mol Cell Biol 8, 1309-1318.

Mushegian, A. R., and Koonin, E. V. (1996). A minimal gene set for cellular life derived by comparison of complete bacterial genomes. Proc. Natl. Acad. Sci. USA 93, 10268-10273.

Nguyen, C., Rocha, D., Granjeaud, S., Baldit, M., Bernard, K., Naquet, P., and Jordan, B. R. (1995). Differential gene expression in the murine thymus assayed by quantitative hybridization of arrayed cDNA clones. Genomics 29, 207-216.

Nishizawa, M., Araki, R., and Teranishi, Y. (1989). Identification of an upstream activating sequence and an upstream repressible sequence of the pyruvate kinase gene of the yeast *Saccharomyces cerevisiae*. Mol Cell Biol 9, 442-451.

Renauld, H., Aparicio, O. M., Zierath, P. D., Billington, B. L., Chhablani, S. K., and Gottschling, D. E. (1993). Silent domains are assembled continuously from the telomere and are defined by promoter distance and strength, and by SIR3 dosage. Genes Dev 7, 1133-1145.

Rose, M. D., Winston, F., and P. Hieter. (1990). Methods in Yeast Genetics. (Cold Spring Harbor, N.Y.: Cold Spring Harbor Laboratory Press), pp. 177.

Schena, M., Shalon, D., Davis, R. W., and Brown, P. O. (1995). Quantitative monitoring of gene expression patterns with a complementary DNA microarray. Science 270, 467-470.

Schmitt, H. D., Ciriacy, M., and Zimmermann, F. K. (1983). The synthesis of yeast pyruvate decarboxylase is regulated by large variations in the messenger RNA level. Mol Gen Genet 192, 247-252.

Sikorski, R. S., and Hieter, P. (1989). A system of shuttle vectors and yeast host strains designed for efficient manipulation of DNA in *Saccharomyces cerevisiae*. Genetics 122, 19-27.

Singh, A., Chen, E. Y., Lugovoy, J. M., Chang, C. N., Hitzeman, R. A., and Seeburg, P. H. (1983). *Saccharomyces cerevisiae* contains two discrete genes coding for the alpha-factor pheromone. Nucleic Acids Res 11, 4049-4063.

Smith, M. M., and Murray, K. (1983). Yeast H3 and H4 histone messenger RNAs are transcribed from two non-allelic gene sets. J Mol Biol 169, 641-661.

St John, T. P., and Davis, R. W. (1979). Isolation of galactose-inducible DNA sequences from *Saccharomyces cerevisiae* by differential plaque filter hybridization. Cell 16, 443-452.

Velculescu, V. E., Zhang, L., Vogelstein, B., and Kinzler, K. W. (1995). Serial analysis of gene expression. Science 270, 484-487.

Zaret, K. S., and Sherman, F. (1982). DNA sequence required for efficient transcription termination in yeast. Cell 28, 563-573.

LENGTHY TABLES

The patent contains a lengthy table section. A copy of the table is available in electronic form from the USPTO web site (http://seqdata.uspto.gov/?pageRequest=docDetail&DocID=US07504493B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07504493B2). An electronic copy of the "Sequence Listing" will also be available from the USPTO upon request and payment of the fee set forth in 37 CFR 1.19(b)(3).

The invention claimed is:

1. An array of probes on a solid support for detecting gene expression, wherein at least one probe comprises at least 18 contiguous nucleotides of SEQ ID NO:12,223 (NORF 5), wherein the array comprises at least 100 probes, wherein each of the at least 100 probes has a sequence that is different from each other sequence.

2. The array of claim 1 which comprises at least 500 probes, wherein each of the at least 500 probes has a sequence that is different from each other sequence.

3. The array of claim 1 which comprises at least 1,000 probes, wherein each of the at least 1,000 probes has a sequence that is different from each other sequence.

4. An array of probes on a solid support for detecting gene expression, wherein at least one probe comprises at least 25 contiguous nucleotides of SEQ ID NO:12,223 (NORF 5).

5. An array of probes on a solid support for detecting gene expression, wherein at least one probe consists of at least 18 contiguous nucleotides of SEQ ID NO:12,223 (NORF 5), wherein the array comprises at least 100 probes, wherein each of the at least 100 probes has a sequence that is different from each other sequence.

6. The array of claim 5 which comprises at least 500 probes, wherein each of the at least 500 probes has a sequence that is different from each other sequence.

7. The array of claim 5 which comprises at least 1,000 probes, wherein each of the at least 1,000 probes has a sequence that is different from each other sequence.

8. An array of probes on a solid support for detecting gene expression, wherein at least one probe consists of at least 25 contiguous nucleotides of SEQ ID NO:12,223 (NORF 5).

* * * * *